United States Patent [19]
Van Reis et al.

[11] Patent Number: 6,027,650
[45] Date of Patent: Feb. 22, 2000

[54] ADSORPTION CHROMATOGRAPHY

[75] Inventors: Robert D. Van Reis, Redwood City; Gerardo A. Zapata, Foster City, both of Calif.

[73] Assignee: Genentech, Inc., South San Francisco, Calif.

[21] Appl. No.: 09/250,976

[22] Filed: Feb. 16, 1999

Related U.S. Application Data
[60] Provisional application No. 60/075,202, Feb. 18, 1998.

[51] Int. Cl.$^7$ .................................................. B01D 15/08
[52] U.S. Cl. ...................... 210/656; 210/198.2; 530/413; 530/417
[58] Field of Search .................................. 210/635, 656, 210/659, 198.2; 530/413, 417

[56] References Cited

U.S. PATENT DOCUMENTS

| | | | |
|---|---|---|---|
| 4,411,789 | 10/1983 | Liburdy | 210/198.2 |
| 4,675,113 | 6/1987 | Graves | 210/635 |
| 5,084,184 | 1/1992 | Burns | 210/656 |
| 5,522,993 | 6/1996 | Carlsson | 210/656 |

FOREIGN PATENT DOCUMENTS

| | | | |
|---|---|---|---|
| 554534 | 8/1993 | European Pat. Off. | 210/656 |
| 699687 | 3/1996 | European Pat. Off. | 210/656 |
| WO 92/18237 | 10/1992 | WIPO | 210/656 |
| WO 96/20798 | 11/1992 | WIPO | 210/656 |
| WO 95/19181 | 7/1995 | WIPO | 210/656 |
| WO 95/23865 | 9/1995 | WIPO | 210/656 |
| WO 96/30046 | 10/1996 | WIPO | 210/656 |
| WO 96/32478 | 10/1996 | WIPO | 210/656 |

OTHER PUBLICATIONS

Carter et al., "Humanization of an anti–p185$^{HER2}$ antibody for human cancer therapy" *Proc. Natl. Acad. Sci.* 89:4285–4289 (1992).

Chang and Chase, "Ion exchange purification of G6PDH From Unclarified Yeast Cell Homogenates Using Expanded Bed Adsorption" *Biotechnology and Bioengineering* 49:204–216 (1996).

Chang et al., "Development of an expanded bed technique for an affinity purification of G6PDH from unclarified yeast cell homogenates" *Biotechnology and Bioengineering* 48:355–366 (1995).

Draeger et al., "Liquid fluidized bed adsorption of protein in the presence of cells" *Bioseparation* 2(2):67–80 (1991).

Fischer et al., "Reduction of Graft Failure by a Monoclonal Antibody (Anti–LFA–1 CD11a) After HLA Nonidentical Bone Marrow Transplantation in Children with Immunodeficiencies, Osteopetrosis, and Fanconi's Anemia" *Blood* 77(2):249–256 (Jan. 15, 1991).

Hourmant et al., "Administration of an Anti–CD11a Monoclonal Antibody in Recipients of Kidney Transplantation" *Transplantation* 58(3):377–380 (Aug. 1994).

Kim et al., "The Vascular Endothelial Growth Factor Proteins: Identification of Biologically Relevant Regions by Neutralizing Monoclonal Antibodies" *Growth factors* 7(1):53–64 (1992).

Liu et al., "Production of a Mouse–Human Chimeric Monoclonal Antibody to CD20 with Potent Fc–Dependent Biologic Activity" *J. Immunol.* 139:3521–3526 (1987).

Maloney et al., "Phase I Clinical Trial Using Escalating Single–Dose Infusion of Chimeric Anti–CD20 Monoclonal Antibody (IDEC–C2B8) in Patients With Recurrent B–Cell Lymphoma" *Blood* 84:2457–2466 (1994).

(List continued on next page.)

*Primary Examiner*—Ernest G. Therkorn
*Attorney, Agent, or Firm*—Deirdre L. Conley

[57] ABSTRACT

The present invention relates to methods useful for purifying materials using adsorbent chromatography, preferably in an expanded bed or packed bed configuration without the need to use a moving packed bed adapter, thereby improving elution characteristics for the sample molecule of interest.

31 Claims, 7 Drawing Sheets

OTHER PUBLICATIONS

Pharmacia Biotech *Expanded Bed Adsorption: Principles and Methods* (ISBN 91–630–5519–8), AA edition pps. 1–160 undated.

Presta et al., "Humanization of an Antibody Directed Against IgE" *J. Immunol.* 151(5):2623–2632 (Sep. 1, 1993).

Scopes, R., "Separation in Solution" *Protein Purification: Principles and Practice,* Chapter 8, pps. 242–249 (1994).

St. John et al., "Immunologic Therapy for ARDS, Septic Shock, and Multiple–Organ Failure" *Chest* 103:932–943 (1993).

Stoppa et al., "Anti–LFA1 Monoclonal Antibody (25.3) for Treatment of Steroid–resistant Grade III–IV Acute Graft–versus–host Disease" *Transplant International* 4:3–7 (1991).

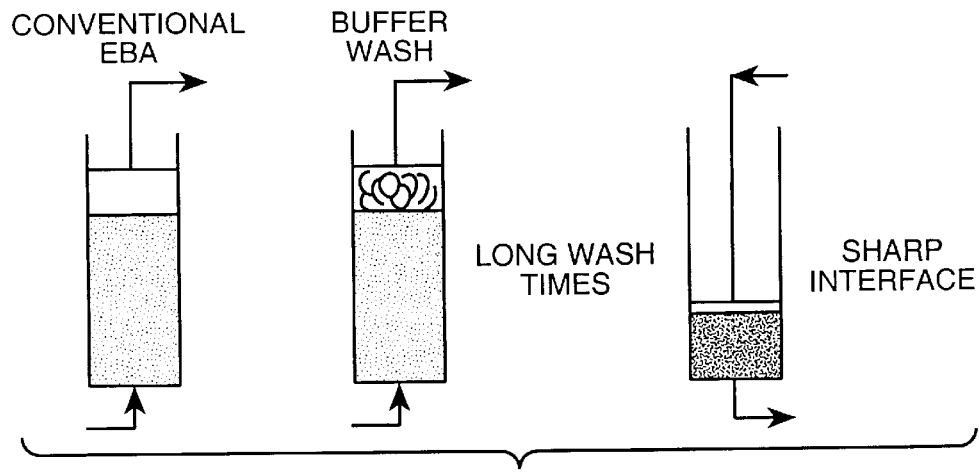
FIG._1A
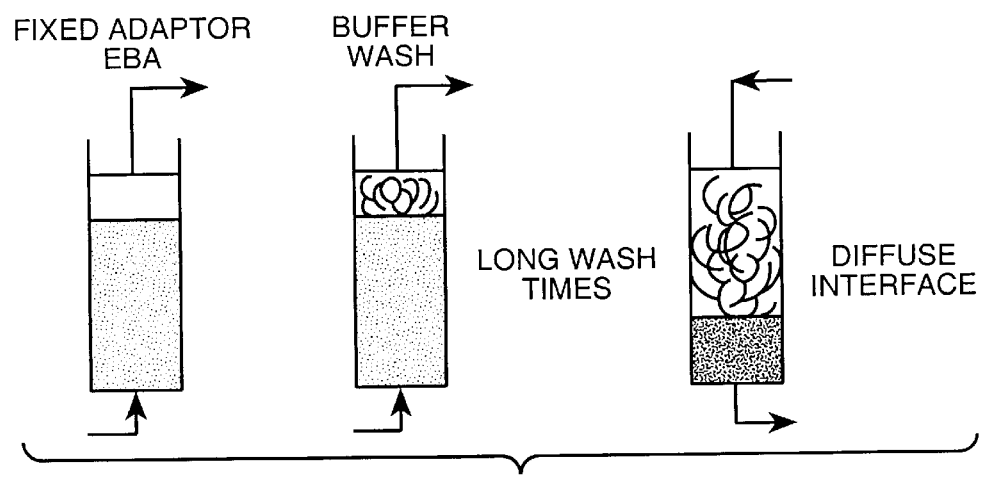
FIG._1B
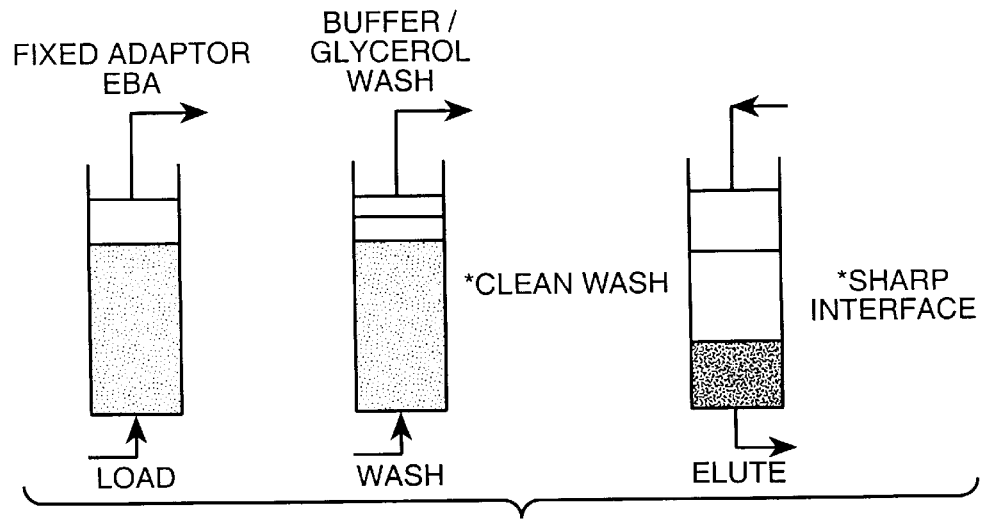
FIG._1C

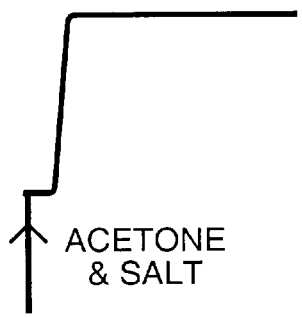
FIG._2A
FIG._2B
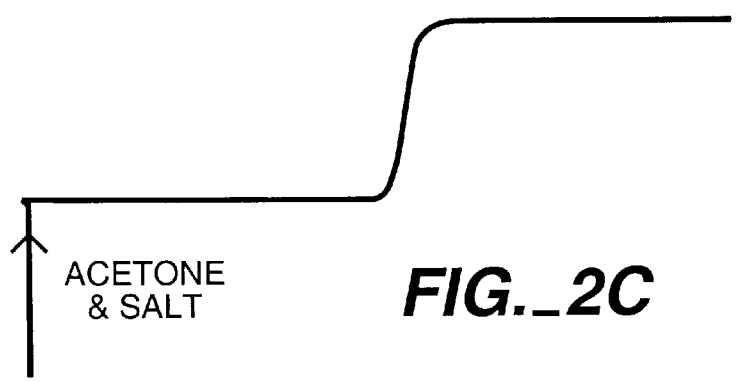
FIG._2C

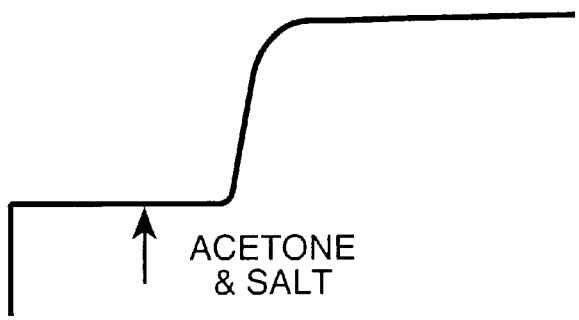
FIG._3A
FIG._3B
FIG._3C

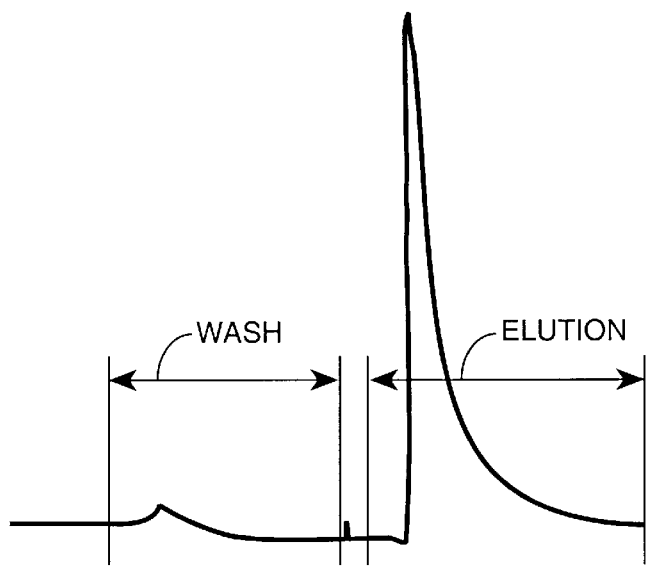
FIG._4A
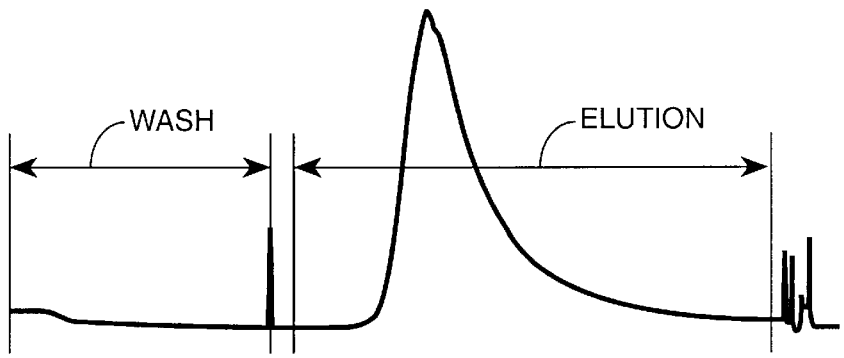
FIG._4B
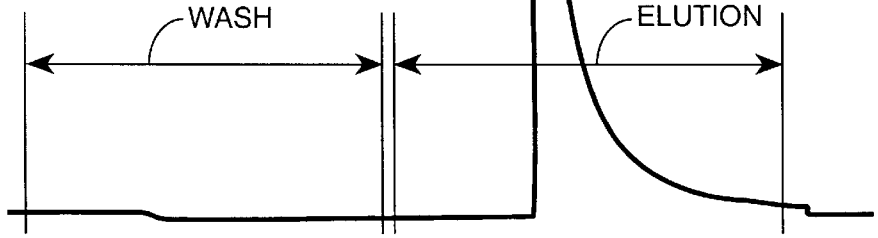
FIG._4C

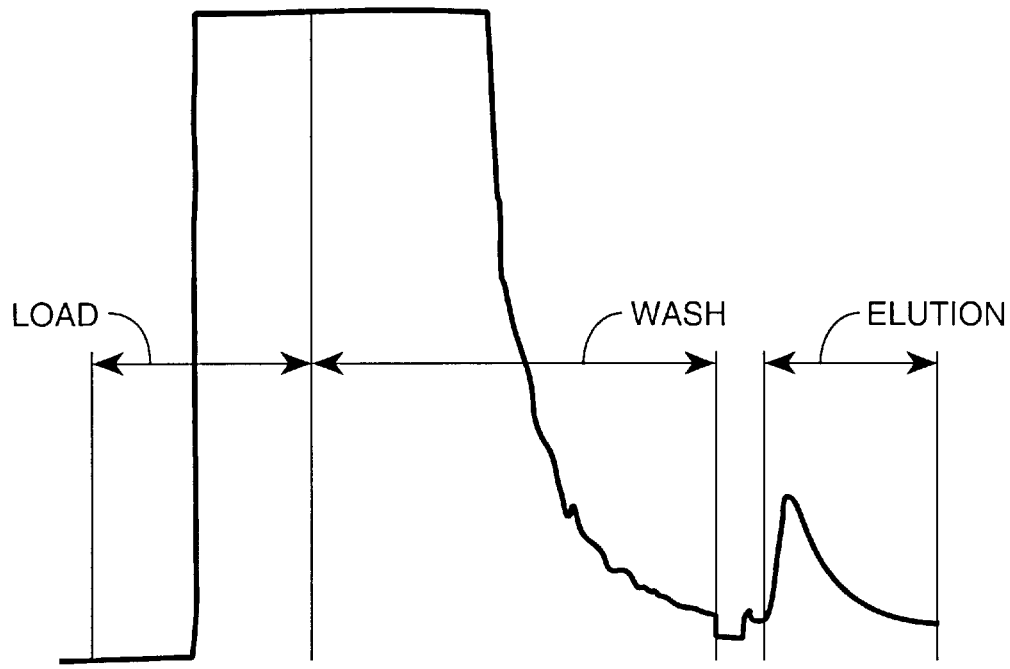
FIG._5A
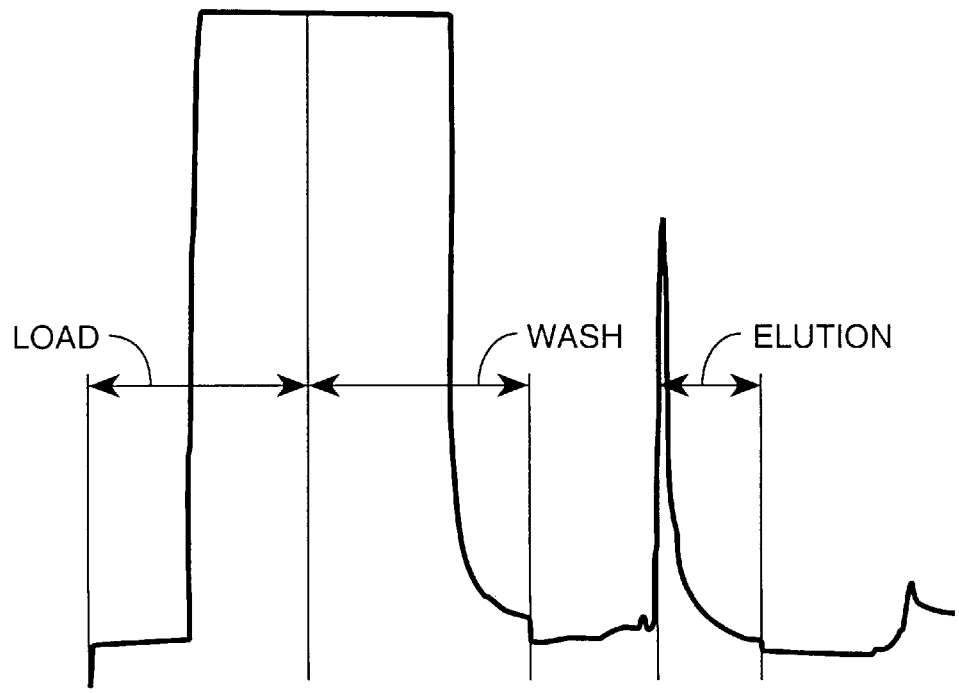
FIG._5B

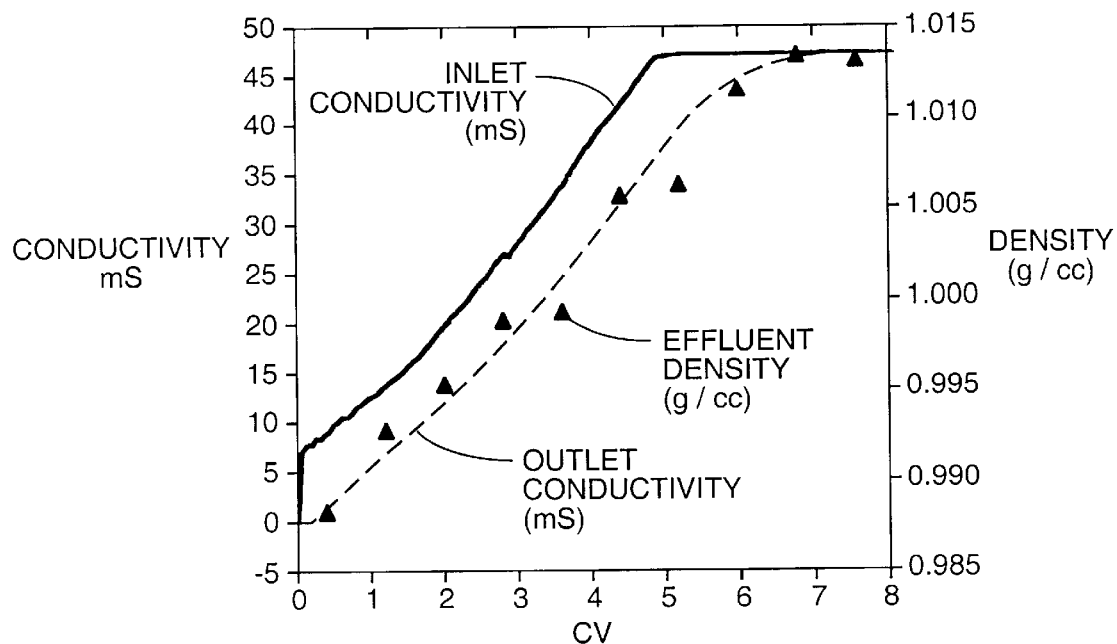
FIG._6A
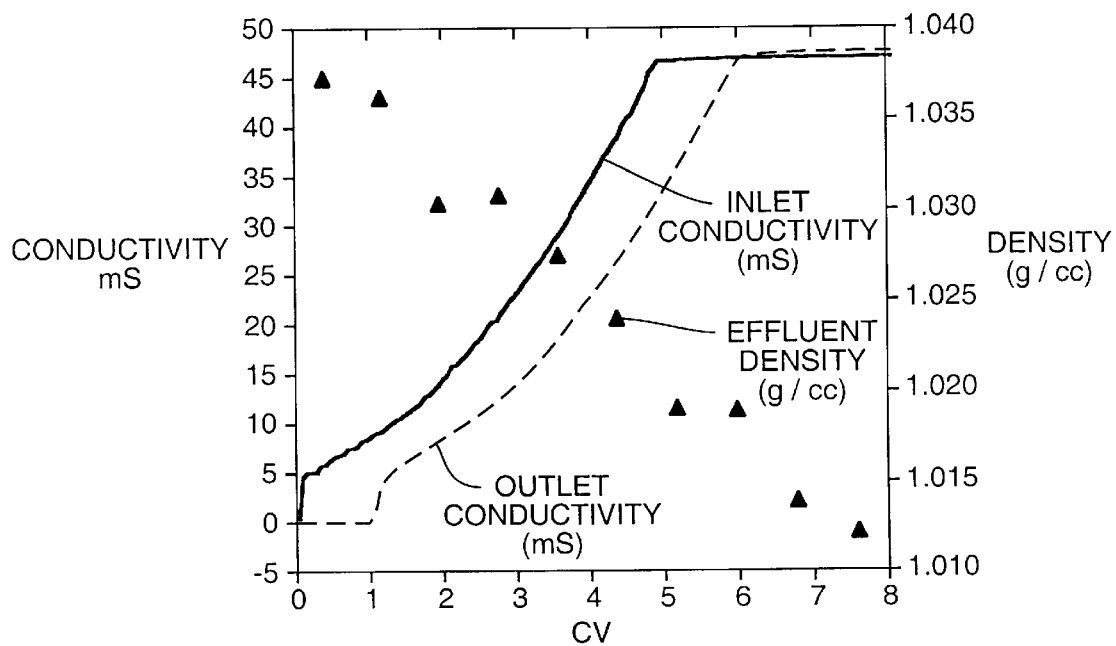
FIG._6B

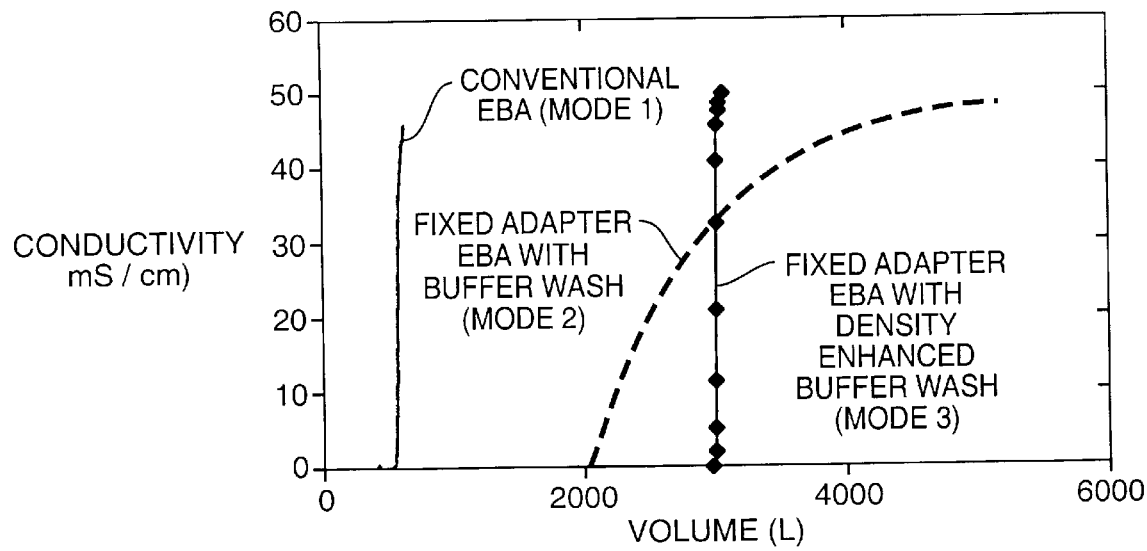
FIG._7
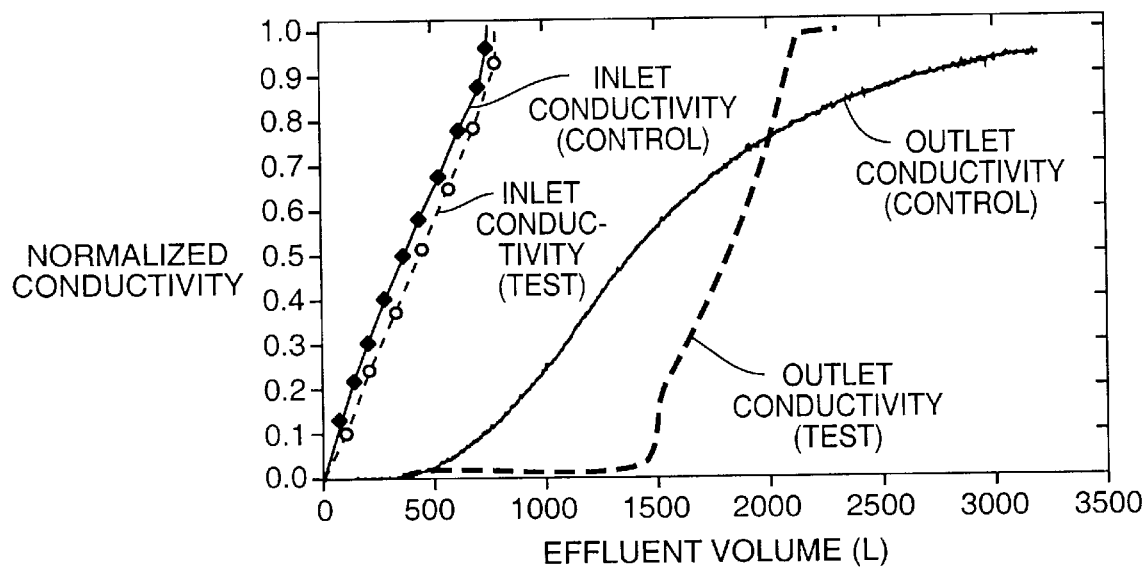
FIG._8

ADSORPTION CHROMATOGRAPHY

RELATED APPLICATIONS

This application is a non-provisional application filed under 37 CFR 1.53(b)(1), claiming priority under 35 USC 119(e) to provisional application Ser. No. 60\075,202 filed Feb. 18, 1998, the contents of which are incorporated herein by reference.

FIELD OF THE INVENTION

The present invention relates to methods useful for purifying materials using adsorbent chromatography, preferably in an expanded bed or packed bed configuration without the need to use a moving packed bed adapter, thereby improving elution characteristics for the sample molecule of interest.

BACKGROUND OF THE INVENTION

The majority of biotechnology processes for producing pharmaceutical or diagnostic products involve the purification of proteins and peptides from a variety of sources. Those include bacteria, yeast and mammalian cell culture fluids, or extracts from naturally occurring tissue (Expanded Bed Adsorption: Principles and Methods, Pharmacia Biotech, ISBN 91-630-5519-8).

The initial purification of a protein or peptide is often via the use of adsorption chromatography on a conventional packed bed of solid support adsorbent. This frequently requires clarification of the crude cell culture or tissue mixture before application onto the chromatography column (Pharmacia Biotech, supra).

Standard techniques used for removal of cells and/or cell debris include centrifugation and microfiltration, which may be used separately or in combination. Packed bed chromatography is problematic in that clogging of the bed occurs readily when passing crude material over the bed, making prechromatographic centrifugation and/or microfiltration necessary and adding to the time and cost of product recovery. Batch adsorption chromatography is a one-step adsorption process of the protein product to a resin in a stirred tank. However, batch adsorption requires large amounts of resin, thereby greatly increasing the cost of recovery (Pharmacia Biotech, supra).

Expanded bed adsorption (EBA) chromatography is useful for the initial recovery of target proteins from crude feed-stock or cell culture. The process steps of clarification, concentration and initial purification can be combined into one unit operation, providing increased process economy due to a decreased number of process steps, increased yield, shorter overall process time, reduced labor cost, and reduced materials cost. In EBA chromatography an adsorbent is expanded and equilibrated by applying an upward liquid flow to the column (see FIG. 1). A stable fluidized bed is formed when the adsorbent particles are suspended in equilibrium due to the balance between particle sedimentation velocity and upward liquid flow velocity. During this phase column adapter is positioned in the upper part of the column and a crude cell mixture is applied to the expanded bed with an upward flow. Target proteins in the mixture are bound to the adsorbent while cell debris and other contaminants pass through unhindered. Weakly bound material is washed from the expanded bed using upward flow of a wash buffer. Cell debris and suspended solids in the column may be flushed to prevent contamination of the elution pool by particulate material (Draeger, N. M. and Chase, H. A., Bioseparation 2:67–80 (1991); Chang, Y. K. et al., Biotechnology and Bioengineering, 48:355–366 (1995); and Chang, Y. K. and Chase, H. A., Biotechnology and Bioengineering, 49:204–216 (1996)).

Following a wash step, flow through the column is stopped and the adsorbent is allowed to settle in the column. The column adapter is then lowered to the surface of the sedimented bed. Flow is reversed and the captured proteins are eluted from the sedimented bed using an appropriate buffer. The eluate contains the target protein in a reduced elution pool volume, partially purified in preparation for packed bed chromatography (Pharmacia Biotech, supra). Flow reversal during protein purification was used to minimize sample band diffusion after loading a dense sample solution (such as an ammonium sulfate protein precipitate) onto a column, but inconveniently required actual inversion of the column to change the direction of flow through the column (Scopes, Robert K., Ch. 8, "Separation in Solution," in Protein Purification: Principles and Practice, Springer-Verlag, NY (1994), pp. 242–249).

There is a need for a simple, cost-effective method to reduce elution pool volume, increase purity of a sample molecule collected from a chromatographic method and increase the concentration of the sample molecule as it is collected from a chromatographic method without, for example, waiting for the adsorbent bed to settle, without a need for a moving column adapter, and without manual column inversion. Such a method would save equipment costs and time for sample purification while improving the level of purity of the target protein or peptide.

SUMMARY OF THE INVENTION

The invention disclosed herein provides for a chromatographic method, preferably a fixed adapter expanded bed adsorption chromatography method, without a need for adsorbent settling, column inversion, or a need for a movable adapter to pack the adsorbent bed. The method of the invention is preferably an improvement of a control process, wherein the improvement is, for example, reduced elution pool volume, increased purity of a sample molecule, and increased concentration of a sample molecule as it is collected from the chromatographic method.

In one aspect, the invention involves a chromatographic method, the method comprising contacting with a solid support, preferably in a vertical column, a first liquid containing a sample molecule and having a first density; contacting with the first liquid a second liquid having a second density; flowing the liquids through the solid support; and collecting the sample molecule in an elution pool volume; wherein the second liquid follows the first liquid and remains in contact with the first liquid. Where the density of the first liquid is greater than the density of the second liquid, the flow of the second liquid into the first liquid is preferably downward in the vertical column. Where the density of the second liquid is greater than the density of the first liquid, the flow of the second liquid into the first liquid is preferably upward in the vertical column. In each embodiment of the invention, an interface between the first and second liquids forms such that mixing of the liquids at the interface is minimized. The method of the invention is useful for reducing the elution pool volume for a sample molecule in a chromatographic process Preferably, the sample molecule elution pool volume is less than approximately 80% of the elution pool volume, preferably less than 70% of the elution pool volume of the sample molecule in a control analysis in which mixing at the interface of the two liquids occurs, such as when the density of the first liquid is less than the density of the second liquid if flow is downward, and the density of the second liquid is less than the density of the first liquid if the flow is upward.

In an embodiment of the invention, the first liquid is a solution comprising a sample molecule and the second liquid is an eluent. Preferably, the density of the solution comprising the sample molecule is greater than the density of the eluent (second liquid), the flow of sample solution is upward, and elution is downward.

In another embodiment of the invention, the density of the first liquid is at least approximately 0.3% greater than the density of the second liquid. Preferably, the density of the first liquid is at least approximately 1% greater than the density of the second liquid. Preferably the first liquid comprises a density increasing agent such as, without limitation, glycerol, a salt, a sugar, ethanol and the like. Where the density increasing agent is typically a solid material, such as a salt or sugar, the upper limit of the density of the first liquid is the density of a solution at the solubility limit of the agent. Where the density increasing agent is typically a liquid, such as ethanol or glycerol, the upper limit of the density of the first liquid is the density of the pure agent.

In another aspect, the invention involves a chromatographic method, the method comprising contacting with a solid support, preferably in a vertical column, a first liquid containing a sample molecule and having a first density; contacting with the first liquid a second liquid having a second density; flowing the liquids through the solid support such that the second liquid follows the first liquid; contacting the second liquid with a third liquid having a third density; flowing the third liquid through the solid support such that the third liquid follows the second liquid; and collecting the sample molecule in an elution pool volume. Where the density of the second liquid is greater than the density of the third liquid, the flow of the third liquid into the second liquid is preferably downward. Where the density of the second liquid is less than the density of the third liquid, the flow of the third liquid into the second liquid is preferably upward. Preferably the chromatographic method is an improvement over a control method, where the improvement is, for example, reduced elution pool volume, increased purity of the sample molecule as it is collected from the chromatographic process, and/or increased concentration of the sample molecule as it is collected from the chromatographic process. Preferably, the sample molecule elution pool volume is less than approximately 80% of the elution pool volume, more preferably less than approximately 70% of the elution pool volume of the sample molecule in a control process in which mixing at the interface of the second and third liquids occurs, such as when the density of the second liquid is less than the density of the third liquid if flow is downward, and the density of the third liquid is less than the density of the second liquid if the flow is upward.

In an embodiment of the invention, the first liquid is a solution comprising a sample molecule, the second liquid is a wash solution, and the third liquid is an eluent. Preferably, the density of the wash solution (second liquid) is greater than the density of the eluent (third liquid), the flow of wash solution is upward and elution is downward.

In another embodiment of the invention in which the flow of wash, the density of the second liquid is at least approximately 0.3% greater than the density of the third liquid. Preferably, the density of the second liquid is from approximately 1% greater than the density of the third liquid. Preferably the second liquid comprises a density increasing agent such as, without limitation, glycerol, a salt, a sugar, and the like. Where the density increasing agent is typically a solid material, such as a salt or sugar, the upper limit of the density of the first liquid is the density of a solution at the solubility limit of the agent. Where the density increasing agent is typically a liquid, such as ethanol or glycerol, the upper limit of the density of the first liquid is the density of the pure agent.

BRIEF DESCRIPTION OF THE DRAWINGS

FIGS. 1A–1C are diagrams illustrating, respectively, conventional expanded bed adsorption (EBA) chromatography (FIG. 1A); Fixed Adapter EBA utilizing a buffer wash in which the density of the wash buffer is less than the density of the elution buffer (FIG. 1B) as in FIG. 1A; and Fixed Adapter EBA of the invention (FIG. 1C) utilizing a buffer wash comprising glycerol in which the density of the wash buffer is greater than the density of the elution buffer allowing the formation of a sharp interface between the load and the wash buffer and between the wash buffer and the elution buffer.

FIGS. 2A–2C are profiles (UV absorbance at 280 nm) of acetone in buffer using Column 1 (i.d. 2.5 cm) in, respectively, Mode 1 (conventional expanded bed adsorption (EBA) chromatography); Mode 2 (fixed adapter EBA with buffer wash); and Mode 3 (fixed adapter EBA with glycerol wash). Specifically, FIG. 2A is a profile generated using a buffer consisting of 25 mM MES, 200 mM NaCl, 0.5% acetone, pH 5.9, downward flow, linear velocity 244.5 cm/hr in Column 1 operating in Mode 1, adapter height 18 cm. FIG. 2B is a profile generated using a buffer of 25 mM MES, 200 mM NaCl, 0.5% acetone, pH 5.9, downward flow, linear velocity 244.5 cm/hr in Column 1 operating in Mode 2, adapter height 70 cm. FIG. 2C is a profile generated using a buffer of 25 mM MES, 200 mM NaCl, 0.5% acetone, pH 5.9, downward flow, linear velocity 244.5 cm/hr in Column 1 operating in Mode 3, adapter height 70 cm.

FIGS. 3A–3C are profiles (UV absorbance at 280 nm) of acetone in buffer scaled up to Column 2 (i.d. 20 cm) in, respectively, Modes 1, 2, and 3. Specifically, FIG. 3A is a profile generated of 25 mM MES, 200 mM NaCl, 0.5% acetone, pH 5.9, downward flow, linear velocity 242.7 cm/hr in Column 2 operating in Mode 1, adapter height 19.5 cm. FIG. 3B is a profile generated using a buffer of 25 mM MES, 200 mM NaCl, 0.5% acetone, pH 5.9, downward flow, linear velocity 242.7 cm/hr in Column 2 operating in Mode 2, adapter height 70.5 cm. FIG. 3C is a profile generated using a buffer of 25 mM MES, 200 mM NaCl, 0.5% acetone, pH 5.9, downward flow, linear velocity 242.7 cm/hr in Column 2 operating in Mode 3, adapter height 70.5 cm.

FIGS. 4A–4C are profiles (UV absorbance at 280 nm) of purified protein load (1300 ml of 0.4 mg/ml protein solution) in Column 1 (i.d. 2.5 cm) in, respectively, Modes 1, 2, and 3. Specifically, FIG. 4A is a profile generated by operating in Mode 1, linear velocity 244.5 cm/hr, wash (25 mM MES, pH 5.9), elution (25 mM MES, 125 mM NaCl, pH 5.9, adapter height 18 cm). FIG. 4B is a profile generated by operating in Mode 2, linear velocity 244.5 cm/hr, wash (25 mM MES, pH 5.9), elution (25 mM MES, 125 mM NaCl, pH 5.9, adapter height 70 cm). FIG. 4C is a profile generated by operating in Mode 3, linear velocity 244.5 cm/hr, wash (25 mM MES, 5% glycerol (v/v), pH 5.9), elution (25 mM MES, 125 mM NaCl, pH 5.9, adapter height 70 cm).

FIGS. 5A–5B are profiles (UV absorbance at 280 nm) of crude feedstock load (600 ml of 0.22 mg/ml protein solution) using Column 1 (i.d. 2.5 cm) in, respectively, Modes 2 and 3. Specifically, FIG. 5A is a profile generated by operating in Mode 2, linear velocity 244.5 cm/hr, wash (25 mM MES, pH 5.9), elution (25 mM MES, 125 mM NaCl, pH 5.6, adapter height 70 cm). FIG. 5B is a profile generated by operating in Mode 3, linear velocity 244.5 cm/hr, wash (25 mM MES, 5% glycerol (v/v), pH 5.9), elution (25 mM MES, 125 mM NaCl, pH 5.6, adapter height 70 cm).

FIGS. 6A–6B are graphs showing changes in eluent conductivity (mS/cm) and density (g/ml, triangles) as a function of column volumes (CV) of eluent passing through the column. Conductivity was monitored at the column inlet (solid line) and the column outlet (dashed line). FIG. 6A is a graph of the results for a salt gradient (0–0.5 M NaCl) run without density control in Column 3. FIG. 6B is a graph of the results for a salt gradient (0–0.5 M NaCl) run with density control (15% glycerol (v/v)).

FIG. 7 is a graph showing eluent conductivity profiles (mS/cm) of downward flow step elution with 0.5 M NaCl eluent flowing at a linear velocity of 100 cm/hr in Column 4. The solid line represents operation in Mode 1 (adapter height 14 cm); the dashed line represents operation in Mode 2 (adapter height 100 cm); and the diamonds represent operation in Mode 3 (adapter height 100 cm).

FIG. 8 is a graph showing the inlet and outlet conductivity profiles (normalized relative to the conductivity of 0.5 M NaCl) as a function of eluent volume for a downward flow salt gradient from 0–0.5 M NaCl at a linear velocity of 100 cm/hr in Column 4 (adapter height was 100 cm). The closed circles trace the inlet conductivity change and the solid line traces the outlet conductivity change for the control run (without density control). The open circles trace the inlet conductivity change and the dashed line traces the outlet conductivity change for the test run (with density control, 15% glycerol (v/v)).

DESCRIPTION OF THE EMBODIMENTS

Definitions

As used herein, the terms "solid support," "adsorbent," "resin," and the like refer to chromatographic material immiscible with the liquid chromatographic phase and upon which the sample molecule interacts by affinity, ionic interaction, hydrophobic interaction, or by chemical reaction, such as enzymatic reaction, that alters the chemical make-up of the sample molecule.

As used herein, the term "sample molecule" includes any molecule that may be processed by the chromatographic method of the invention. Preferably, the sample molecule is a biological entity of natural biological or biochemical origin or produced by biological or biochemical processes, or by recombinant DNA processes. Examples of preferred sample molecules include, but are not limited to mammalian cells and microorganisms such as bacteria, fungi and yeast, as well as polypeptides, proteins, either naturally or recombinantly produced whether glycosylated or not, cellular components, nucleic acids, viruses, carbohydrates, and other biological molecules of interest. Particularly preferred sample molecules include, but are not limited to, antibodies such as anti-IL-8, St. John et al., (1993) Chest 103:932 and International Publication No. WO 95/23865; anti-CD11a, Fischer et al., Blood, 77:249–256(1991), Steppe et al., (1991) Transplant Intl. 4:3–7, and Hourmant et al., (1994) Transplantation 58:377–380; anti-IgE, Presta et al., (1993) J. Immunol. 151:2623–2632, and International Publication No. WO 95/19181; anti-HER2, Carter et al., (1992) Proc. Natl. Acad. Sci. USA 89:4285–4289, and International Publication No. WO 92/20798; anti-VEGF, Jin Kim et al., (1992) Growth Factors, 7:53–64, and International Publication No. WO 96/30046; anti-CD18, International Publication No. WO 96/32478; and anti-CD20, Maloney et al., (1994) Blood, 84:2457–2466, and Liu et al., (1987) J. Immunol., 139:3521–3526.

As used herein, the term "elution pool volume" refers to the volume of the eluate fraction containing the sample molecule, wherein the fraction is collected from the time at which detection of sample molecule elution begins until elution ends. Alternatively, the elution pool volume may be determined from the time at which detection of sample molecule reaches approximately 15% of signal maximum (initiation of the positive step input signal) until the time at which the detection signal drops to approximately 15% of the signal maximum (negative step input signal). In addition, elution pool volume may be measured, for example, by measuring the peak width at, for example, the baseline of the chromatographic trace (see FIGS. 4A–4C and 5A–5B). In still another alternative method, elution volume may be determined using a non-adsorbent marker molecule (UV detection of acetone or conductivity detection of a salt in a buffer, as nonlimiting examples), where $C/C_0=0.1$ to $C/C_0=0.9$.

As used herein, the term "control process" refers to a chromatographic process using the same or equivalent apparatus, adsorbent, sample molecule, and liquids (such as buffers) as used in the method of the invention. However, the control process differs from a process of the invention primarily in that in the process of the invention a first and second liquid or a second and third liquid differ in a property (such as density) that affects mixing of the liquids during flow through the column, but does not differ in the control process. Consequently, in the control process mixing occurs at the interface between the two liquids as they flow through the solid support material, resulting in a larger elution pool volume for the sample molecule, but such mixing is minimized in the process of the invention. Where the chromatographic process comprises a load buffer (first liquid), a wash buffer (second liquid), and an elution buffer (third liquid), preferably the wash buffer is a higher density than either the load buffer or the elution buffer and mixing at the interface between the solutions is minimized. Preferably, the wash buffer is at least approximately 0.3% greater than the densities of either the load buffer or the elution buffer. Where the density increasing agent is typically a solid material, such as a salt or sugar, the upper limit of the density of the first liquid is the density of a solution at the solubility limit of the agent. Where the density increasing agent is typically a liquid, such as ethanol or glycerol, the upper limit of the density of the first liquid is the density of the pure agent.

As used herein, the term "chromatography" and like terms refer to a form of chromatography in which a solid adsorbent material is contacted with a sample molecule in a liquid, and the sample molecule interacts the solid material as the liquid passes through the solid adsorbent material (such as by the non-limiting examples of ion exchange, affinity, and size exclusion chromatography). The term "chromatography assay or process" and like terms refer to such non-limiting examples as expanded bed column chromatography, packed bed chromatography, packed bed reactors (wherein a reactive molecule such as an enzyme is covalently attached to the solid support), and membrane chromatography.

MODES OF CARRYING OUT THE INVENTION

In one embodiment of the invention involving two liquids, the first liquid comprises glycerol, wherein the glycerol content is varied to generate a density of the first liquid that is greater than the density of the second liquid. Preferably, the density of the first liquid is at least approximately 0.3% greater than the density of the second liquid. More preferably, the density of the first liquid is from approximately 1% greater than the second liquid up to approximately the density of a solution at the solubility limit of a typically solid density increasing agent, or up to the density of the pure liquid of a liquid density increasing agent. In another embodiment, a solute such as salt, ethanol, sugar (such as glucose), or other molecule is added to the first liquid to alter its density such that the density of the first liquid is greater than the density of the second liquid. The first, denser liquid is preferably a wash buffer and flows through the solid support in an upward direction; the second, less dense liquid is preferably an eluent that flows downward through the solid support within in the column.

In another embodiment of the invention involving three liquids, the first liquid comprises a sample molecule, the second liquid comprises glycerol, wherein the glycerol content is varied to generate a density of the second liquid that is greater than the density of the third liquid, and optionally greater than the density of the first liquid. Preferably, the density of the second liquid is at least approximately 0.3% greater than the density of the third liquid. More preferably, the density of the second liquid is from approximately 1% greater than the density of the third liquid. In another embodiment, a solute such as salt, ethanol, sugar (such as glucose), or other molecule is added to the second liquid to alter its density such that the density of the second liquid is greater than the density of the third liquid up to a density approximately equal to the density of a solution at the solubility limit of a typically solid density increasing agent, or up to approximately the density of the pure liquid density increasing agent. The second, denser liquid is preferably a wash buffer and flows through the solid support in an upward direction; the third, less dense liquid is preferably an eluent that flows downward through the solid support within in the column.

In still another embodiment of the invention, the chromatographic process is column chromatography and the solid support is a particulate. Preferably the particulate is a resin, a glass bead, or a carbohydrate backbone material that forms a solid support for chromatography.

In yet another embodiment of the invention the chromatography solid support is a porous membrane. A porous membrane useful in the practice of the invention includes, but is not limited to, microporous and macroporous membranes made from regenerated cellulose, polyvinylidene fluoride, nylon, and polysulfone.

In another embodiment of the invention the sample molecule elution pool volume is less than approximately 80% of the elution pool volume of the sample molecule, preferably less than approximately 70% of the elution pool volume of the sample molecule in the control chromatography. The control chromatography, which does not comprise density control to minimize mixing of the solutions in the column, uses the same or equivalent apparatus for measuring the elution pool volume of the sample molecule. In still another embodiment, the sample molecule elution pool volume is preferably between approximately 50–80% of the elution pool volume of the sample molecule in the control process.

In another embodiment of the invention, where the chromatography utilizes a first, second and third liquid, the direction of flow of the third liquid is opposite the direction of flow of the first and second liquids.

In an embodiment of the invention comprising first, second and third liquids, the second liquid comprises glycerol, wherein the glycerol alters the density of the second liquid such that its density is greater than the density of the third liquid. Preferably, the density of the second liquid is at least approximately 0.3% greater than the density of the third liquid. More preferably, the density of the second liquid is approximately 1% greater than the density of the third liquid. Where the density increasing agent is typically a solid material, such as a salt or sugar, the upper limit of the density of the first liquid is the density of a solution at the solubility limit of the agent. Where the density increasing agent is typically a liquid, such as ethanol, the upper limit of the density of the first liquid is the density of the pure agent.

In an embodiment of the invention comprising a first and second liquid or the invention comprising a first, second and third liquid, at least one of the liquids may comprise a gradient, wherein the concentration of a species within the liquid is varied over time, thereby altering its density over time. In such a situation, a density-altering agent (such as glycerol, salt, sugar or the like) may be added such that the density of the gradient liquid remains constant or is decreasing (for downward elution) or increasing (for upward elution) relative to the density of a different liquid with which it is in contact. In a nonlimiting example, where a third liquid comprises a salt gradient of increasing density, glycerol may be added at an initial concentration and reduced throughout the gradient as the salt concentration is increased, thereby maintaining a substantially constant (or decreasing) density for the third liquid. The gradient may be a continuous gradient or a step gradient.

Embodiments of each aspect of the invention may be utilized in an expanded bed configuration without the need for a moving bed adapter apparatus.

An embodiment of each aspect of the invention includes altering the density of a liquid used in the invention by adding glycerol as the density-altering agent. In this embodiment, a liquid of the invention comprises glycerol at a concentration from approximately 2.5% glycerol to approximately 25% glycerol. Preferably, the glycerol concentration is from approximately 5% glycerol to approximately 15% glycerol. More preferably, the glycerol concentration is adjusted to alter the density of the liquid such that it is at least approximately 0.3% greater than another liquid of the invention. For example, if the liquid comprising glycerol is the wash buffer, then its density is greater than the density of the load buffer and elution buffer of the invention by approximately 0.3% up to approximately the density of a glycerol solution at the solubility limit of glycerol in the buffer.

An alternative embodiment of each aspect of the invention includes altering a combination of features of a liquid of the process of the invention (e.g. altering the density of the wash solution) is also possible. Preferably, density is altered such that the contacting liquids form an interface such that mixing between the contacting liquids is minimized as the liquids flow through the adsorbent material.

All references cited herein are incorporated herein by reference in their entireties. Before the present methods for purifying a sample molecule in expanded bed adsorption chromatography without using a moving bed adapter are described, it is to be understood that this invention is not limited to the particular samples or methods described as such samples and methods may, of course, vary. It is also to be understood that the terminology used herein is for the purpose of describing particular embodiments only, and is not intended to be limiting since the scope of the present invention will be limited only by the appended claims.

The following examples are set forth so as to provide those of ordinary skill in the art with a complete disclosure and description of how to make the compounds and compositions of the invention and are not intended to limit the scope of what the inventors regard as their invention. Efforts have been made to insure accuracy with respect to number used (e.g. amounts, temperature, etc.), but some experimental errors and deviation should be accounted for.

EXAMPLES

The fixed adapter EBA process eliminates the need for a moving top adapter which is essential in the operation of a conventional EBA process. Thus, the fixed adapter EBA process of the invention may be performed at lower cost and with greater convenience than conventional EBA.

In a typical EBA process, protein capture takes place when the protein solution is pumped into the column in an upward direction, thereby expanding the packed column bed. Subsequently the column is washed with a wash solution, which also flows in the upward direction, while the protein of interest is retained by the solid support. Protein elution takes place when the eluent is pumped in the downward direction, which packs the column. In a conventional EBA, the top adapter is moved down close to the packed bed before elution begins. This is done so as to minimize the void volume above the packed bed, since the presence of void volume could lead to mixing and dilution of the eluent.

In a fixed adapter EBA, however, the need for a moving adapter is eliminated by introducing a density-altering agent (e.g., glycerol) in the wash solution. This minimizes mixing of solutions in the column, such as when a denser wash buffer flows upward displacing a less dense load buffer, or when a less dense eluent flows downward displacing a denser wash buffer.

The Expanded Bed Adsorption (EBA) setup was used to demonstrate this concept, but utilized the adapter in a fixed position. This setup consisted of a STREAMLINE™ column packed with STREAMLINE SP-XL™ resin (cation exchange), Masterflex Pump ™, UV absorbance detector and chart recorder. The column was operated in 3 modes as described in Table 1. The examples provided herein compare the performance of conventional (moving adapter) EBA and the fixed adapter EBA of the invention with and without modification of the wash buffer density.

TABLE 1

Modes of Operation

| Mode | Description | WASH Solution (flow direction) | ELUTION Adapter position (flow direction) |
|---|---|---|---|
| 1 | Conventional EBA | 25 mM MES, pH 5.9 (upward) | Close to the packed bed (downward) |
| 2 | Fixed Adapter EBA with buffer wash | 25 mM MES, pH 5.9 (upward) | Fixed position, same as during load and wash, much above the packed bed surface (downward) |
| 3 | Fixed Adapter EBA with glycerol wash | 25 mM MES, 5% glycerol (v/v), pH 5.9 (upward) | Fixed position, same as during load and wash, much above the packed bed surface (downward) |

Example 1

This Example compares the elution profile of the eluent in the 3 modes described in Table 1. No protein was loaded onto the column. The eluent buffer (25 mM MES, 200 mM NaCl, 0.5% acetone, pH5.9) was pumped through the solid support within the chromatographic column at a linear velocity of 245 cm/hr. The acetone was introduced in the eluent to monitor its flow by recording UV absorbance at 280 nm. The physical parameters of the column used (Column 1) are listed in Table 2.

TABLE 2

Physical Parameters of Column 1 (STREAMLINE 25 ™)

| | |
|---|---|
| Column diameter | 2.5 cm |
| Total Column length | 100 cm |
| Packed bed volume | 85.9 ml |
| Packed bed height | 17.5 cm |
| Top Adapter position during load and wash | 70 cm |
| Top Adapter position during elution (Mode 1) | 18 cm |
| Top Adapter position during elution (Modes 2, 3) | 70 cm |

FIGS. 2A–2C show the UV traces of the eluent in Modes 1, 2 and 3, respectively. It can be seen that in Mode 1 (Conventional EBA (moving adapter), FIG. 2A), the eluent front was sharp, demonstrating plug flow. The eluent profile in Mode 2 (Fixed Adapter EBA with 25 mM MES buffer wash, FIG. 2B) showed considerable mixing of the solutions, as was evident from the amount of time needed for the UV trace of the eluent to reach its maximum. The flow profile of the eluent in Mode 3 (Fixed Adapter EBA with the 25 mM MES, 5% glycerol (v/v) wash, FIG. 2C) had a sharp front similar to that seen in the conventional EBA mode (FIG. 2A), but without use of a movable adapter.

Example 2

The purpose of this experiment was to demonstrate consistent behavior, as observed for Column 1 (i.d. 2.5 cm) in FIGS. 2A–2C, upon scale up to Column 2 (i.d. 20 cm). The physical parameters of Column 2 are listed in Table 3. As in Example 1, no protein was loaded onto the column. The eluent buffer composition was the same as in Example 1 and was pumped through the solid support bed within the column at a linear velocity of 243 cm/hr.

FIGS. 3A–3C show the UV traces of the eluent in Modes 1, 2 and 3, respectively. These profiles were consistent with those observed for Column 1 (FIGS. 2A–2C) and hence the effect showed consistency upon scale-up.

TABLE 3

Physical parameters of Column 2 (STREAMLINE 200 ™)

| | |
|---|---|
| Column diameter | 20 cm |
| Total Column length | 95 cm |
| Packed bed volume | 5746 ml |
| Packed bed height | 18.3 cm |
| Top Adapter position during load and wash | 70.5 cm |
| Top Adapter position during elution (Mode 1) | 19.5 cm |
| Top Adapter position during elution (Modes 2, 3) | 70.5 cm |

Example 3

The results of the experiments in this Example confirm that the process of the invention sharpens the elution profile, reduces the elution pool volume. For this purpose a purified protein, anti-CD 18 in this Example, was loaded onto Column 1 (1300 ml of 0.4 mg/ml protein solution at a linear velocity of 245 cm/hr). After washing the column with the appropriate buffer, as outlined in Modes 1, 2 and 3, the eluent (25 mM MES, 125 mM NaCl, pH 5.9) was pumped downward through the solid support within the column at a linear velocity of 245 cm/hr.

The effluent from the column was monitored at 280 nm to trace the elution profile of the protein, as shown in FIGS. 4A–4C. It can be seen that in the conventional EBA mode (Mode 1, FIG. 4A) and the Fixed Adapter EBA mode with the 25 mM MES, 5% glycerol (v/v) wash (Mode 3, FIG. 4C) elution pool volumes were small (580 ml) and protein concentrations were high. In the Fixed Adapter EBA mode with the 25 mM MES wash (Mode 2, FIG. 4B) elution pool volume was larger (980 ml) and the protein was less concentrated than in Modes 1 and 3. Elution pool volume was determined by measuring the volume eluted from the time peak detection began until the signal returned to baseline. The example thus demonstrates that by using the process of the invention the elution volume of a protein of interest reduced relative to the control process that failed to minimize mixing of the wash solution and the eluent.

Example 4

The objective of this experiment was to demonstrate the effect observed in the previous experiments in an operation of a Fixed Adapter EBA process of the invention, in which process an unpurified feedstream of a protein mixture is introduced onto the solid support bed. For this purpose, frozen *E. coli* paste containing the protein of interest, anti-CD18, was thawed and then slurried in an extraction buffer (25 mM MES, 10 mM MgSO4, pH 5.6) and passed through a pressure homogenizer (5000 psi) to extract the protein. Column 1 was then loaded with this crude feedstock (600 ml of approximately 0.22 mg/ml protein feedstock at a linear velocity of 245 cm/hr). The column was then washed and eluted in Modes 2 and 3. The washing in each mode was continued until the wash effluent was clear. The eluent (25 mM MES, 150 mM NaCl, pH 5.6) was pumped downward through the solid support within the column at a linear velocity of 245 cm/hr.

The UV traces at 280 nm for Modes 2 and 3 are shown in FIGS. 5A and 5B, respectively. The elution profile for protein purification in Modes 2 and 3 from this Example (FIGS. 5A and 5B) had the same characteristics as in Example 3 (FIGS. 4B and 4C). Elution pool volumes were smaller and the protein of interest was more concentrated using Mode 3 (FIG. 5B) than using Mode 2 (FIG. 5A) as shown in Table 4.

TABLE 4

Wash Volumes and Elution Pool Characteristics (Example 4)

| Mode (Figure no.) | Description | Wash Volume | Elution Pool Volume (protein concentration) |
|---|---|---|---|
| Mode 2 (FIG. 5A) | Fixed Adapter EBA with buffer wash | 1100 ml | 540 ml (0.22 mg/ml) |
| Mode 3 (FIG. 5B) | Fixed Adapter EBA with glycerol wash | 600 ml | 300 ml (0.44 mg/ml) |

In addition to generating sharp elution profiles for efficient purification of a protein of interest, the method of the invention also sharpens the load and wash profile of the unwanted proteins present in excess in the load solution. Comparison of FIG. 5A (Mode 2) and FIG. 5B (Mode 3) shows that a wash buffer of greater density than the eluent (FIG. 5B, Mode 3) sharpens the profile of the large peak of unwanted protein. This effect reduces the length of time over which the unwanted proteins are washed from the column and provides improved baseline separation between unwanted proteins and the protein of interest, thereby allowing collection of the protein of interest in a more concentrated and purer form.

Density differences, rather than viscosity differences, between the solutions passed through the column contribute to the improved elution efficiency demonstrated herein. Solution density and viscosity were measured using standard techniques for various solutions used in Mode 2 and Mode 3 analyses as described in this Example. A buffer without density control ("Buffer" in Table 5) and a buffer with density control (for example, a buffer containing glycerol; "Wash (Buffer+5% glycerol (v/v)" in Table 5) were used in Mode 2 and Mode 3, respectively. The Load solution was a bacterial paste homogenate diluted in buffer. All density and viscosity measurements were made at ambient temperature (approximately 23° C.).

TABLE 5

Density and Viscosity of Fixed Adapter EBA Solutions

| Solution | Density (g/ml) | Viscosity (cps) |
|---|---|---|
| Load (*E. coli* paste - 15 × dilution in buffer) | 1.003 | 2.3 |
| Buffer (25 mM MES, 10 mM MgSO4) | 0.9981 | 0.92 |
| Wash (Buffer + 5% glycerol (v/v)) | 1.0123 | 1.09 |
| Eluent (Buffer + 200 mM NaCl) | 1.0067 | 0.95 |

In Mode 3 using the above solutions, the column is loaded in an upward direction with the Load solution having density of 1.003 g/nd and viscosity of 2.3 cps. Next the Wash solution, having a higher density of 1.0123 g/ml and lower viscosity of 1.09 than the Load solution, follows in an upward direction. Finally, the Eluent, having a lower density of 1.0067 g/ml and lower viscosity of 0.95 than the Wash, follows in a downward direction. Only the density of each solution alternates from lower to higher to lower than the solution before it, showing that density differences are responsible for minimization of mixing between the solutions and improved elution efficiency.

The results presented herein show that the addition of a density-altering agent, such as glycerol, in the wash solution of an EBA operation eliminates the need for a moving top adapter in an EBA column during flow of eluent downward through the solid support within the column. These results demonstrate that maintaining the correct order of densities (bottom-higher density, top-lower density) in a fixed adapter EBA process of the invention contributes to a sharp eluent profile in a step elution process.

Example 5

Salt gradients introduced into a fixed adapter EBA column show significant mixing of the gradient solutions. The increasing salt gradient corresponds to an increasing density gradient, which causes mixing in the head space above the packed column bed.

This experiment demonstrates that a gradient, such as an increasing salt gradient, can be used in the fixed adapter EBA process of the invention by adding a density-controlling agent (such as glycerol, sugar, or the like). For example, if a reverse density gradient is established (from higher density to lower density), the gradient shape and gradient length may be preserved by minimizing mixing of solutions within the column. In the present example, the increasing salt gradient was established by washing the column with a wash solution (Solution A, Table 7) and then, during eluent flow in the downward direction, adding increasing amounts of salt solution (Solution B, Table 7). As a control, no density-controlling agent (such as glycerol) was added to Solutions A or B. In the test setup, a density-controlling agent was present in Solution A (15% glycerol (v/v), for example, in this test), but not in Solution B. Preferably, where the density of Solution A (or its equivalent in a different gradient) is at least approximately 0.3% greater than the density of Solution B (or its equivalent), density control is possible. In the present Example, an increasing salt gradient was established simultaneous with the establishment of a decreasing density gradient. The decreasing density gradient meant that a less dense solution was introduced onto a more dense solution as the gradient progressed. The decreasing density gradient minimized mixing of the gradient in the void volume above the packed column bed.

An empty column (Column 3, Table 6) was used to represent the void volume above the packed column in a fixed adapter EBA process. The gradient length established by salt gradients with and without the addition of a density-altering agent was determined by standard techniques as the volume of eluent passing through the column during the gradient. Gradient length was conveniently described in terms of the number of column volumes (CV), where CV is the volume of the chromatographic column used in an experiment. An FPLC system setup (Biosys 2000™, Beckman Instruments Inc., Fullerton Calif.) was used in the experiments described in this Example. The physical parameters of Column 3 are specified in Table 6. The control and test gradients are described in Table 7.

TABLE 6

Physical Parameters of Column 3

| | |
|---|---|
| Height | 65 cm |
| Diameter | 1.6 cm |
| Total Volume | 130 ml |
| Void Volume | 130 ml |

TABLE 7

Salt Gradients With and Without Density Control

| Gradient Description | Solutions |
|---|---|
| Control Run, without density control: Gradient elution from 0–0.5M NaCl | Solution A: 100–0% water Solution B: 0–100% 0.5M NaCl |
| Test Run, with density control: Gradient elution from 0–0.5M NaCl | Solution A: 100–0% 15% glycerol (v/v) Solution B: 0–100% 0.5M NaCl |

CV = 5, where CV = column volume
Linear velocity = 100 cm/hr

The progress of the salt gradient was monitored by measuring conductivity of the eluent at the column inlet and column outlet. FIG. 6A shows the results for the Control increasing salt gradient without density control described in Table 7. The inlet conductivity (solid line) measures increasing salt concentration as the gradient proceeds for a total gradient length of 5 CV (x axis). The gradient increases linearly to a maximum conductivity at which time the line flattens sharply. By contrast, the column outlet conductivity profile indicates mixing of solutions in the column by the positive conductivity at the outlet before 1 CV, an increase in gradient length to 7 CV, and the gradual tapering of the conductivity at the end of the gradient.

Density control minimizes mixing and improves the gradient profile as illustrated in FIG. 6B for the test salt gradient described in Table 7. The outlet conductivity profile spans 5 CV from 1 CV (one void volume) to 6 CV along the x axis, thereby maintaining the 5 CV theoretical gradient length measured at the column inlet. The lack of detectable conductivity at the outlet until 1 CV supports the notion that solution mixing is greatly minimized by controlling the density. In this test process, the density decreases (FIG. 6B, triangles) as the salt concentration increases. The decreasing eluent density reflects the preferred order of introducing solutions into the column when using the process of the invention. According to the invention, when flow is downward through the column the less dense solution is introduced on top of the more dense solution such that the gradient length and profile are as close as possible to the theoretical profile.

Example 6

This Example demonstrates how unmixed reverse gradients (where a reverse gradient is, for example, a salt gradient from higher to lower salt concentration) in the upward flow direction can be produced by glycerol compensation. Since elution in the upward direction does not require a high density wash hence the starting point for this experiment was to completely fill Column 3 with water, which represents the low density wash buffer. Two scenarios are investigated, upward flow of reverse gradients with and without glycerol compensation, as specified in Table 8.

TABLE 8

Scenarios for reverse gradients in the upward flow direction

| Gradient Description | Solutions |
|---|---|
| Control Run, without glycerol compensation: Gradient elution from 0.5–0M NaCl | Solution A: 0–100% water Solution B: 100–0% 0.5M NaCl |
| Test Run, with glycerol compensation: Gradient elution from 0.5–0M NaCl | Solution A: 0–100% 10% glycerol (v/v) Solution B: 100–0% 0.5M NaCl |

Linear velocity = 100 cm/hr; column volume (CV) = 5 CV

The gradient generated by this process was monitored by measuring the conductivity profile of the column effluent as described in Example 5.

Example 7

This Example demonstrates that density control minimizes mixing in large chromatographic columns frequently used in large-scale protein purification using an EBA system. The large EBA column (Column 4, 1.2 m diameter) minimized solution mixing similar to the smaller columns used herein for step and gradient elutions using density control. Column 4 is described in Table 9.

TABLE 9

Physical Parameters of Column 4

| Column Dimensions | |
|---|---|
| Height | 100 cm |
| Diameter | 120 cm |
| Resin height | 14 cm |
| Resin Volume | 158 L |
| Total Column Volume | 1130 L |

Step elution: The modes of step elution are similar to those described in Table 1 except that the low density wash buffer (25 mM MES, pH 5.9) was replaced with water and the high density wash buffer (25 mM MES, 5% glycerol (v/v), pH 5.9) was replaced with 15% glycerol (v/v). The eluent in each of Modes 1–3 was 0.5 M NaCl in water with a downward eluent flow of 100 cm/hr linear velocity. In Modes 2 and 3 the adapter was fixed at 100 cm (top of the column). Conductivity of the eluent was monitored to indicate the sharpness of the eluent profile. FIG. 7 shows that the eluent profiles in the three Modes are consistent with those for smaller columns (see FIGS. 2A–2C and FIGS. 3A–3C).

Gradient elution with and without density control: A control and test gradient similar to those described in Table 8 were used to investigate the efficiency of gradient elution in a large column (Column 4). However, the gradient length in the present experiments was 0.7 CV, a much steeper gradient and likely to cause increased mixing of the gradient solutions. The adapter height was fixed at 100 cm. FIG. 8 shows that the salt gradient formed with density control (test, dashed line) is similar to the inlet conductivity profile suggesting that mixing is minimized in the large column when the densities of the gradient solutions are controlled. However, the outlet conductivity profile for the control gradient (lacking density control) differed noticeably from the inlet conductivity profile because no density control was available to minimize mixing of the gradient solutions, particularly under the combined difficulties of large column volume and steep gradient. This accounts for the gradually tapering curve observed in the control run (no density control) because the steeper gradient encouraged increased mixing of solutions. Improved gradient efficiency due to density control, in which less dense solutions are introduced on top of more dense solutions when flow is downward, is consistent between the results obtained with a large column (FIG. 8) as well as with a small column (FIG. 6B).

The instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure.

What is claimed is:

1. A vertical column chromatographic method, without the need to use a moving packed bed adapter and without column inversion the method comprising:
   a) contacting with a solid support a first liquid containing a sample molecule and having a first physical characteristic;
   b) contacting with the first liquid a second liquid having a second physical characteristic and acts as an eluent of the sample molecule;
   c) flowing the liquids through the solid support; and
   d) collecting the sample molecule in an elution pool volume;
       wherein the second liquid follows the first liquid and remains in contact with the first liquid;
       wherein the physical characteristics of the first and second liquids generate an interface between the first and second liquids and mixing is minimized between the two liquids as they flow through the solid support; and
       wherein the elution pool volume is less than approximately 80% of the elution pool volume of the sample molecule in a control process analysis.

2. The method according to claim 1, wherein the method is an improvement over a control process, the improvement selected from the group consisting of reduced pool elution volume, increased purity of the sample molecule, and increased concentration of the sample molecule.

3. The method according to claim 1, wherein the physical characteristic is density.

4. The method according to claim 3, wherein the density of the first liquid is less than the density of the second liquid, and wherein second liquid flows into the first liquid in an upward direction.

5. The method according to claim 4, wherein the density of the first liquid is at least approximately 0.3% greater than the density of the second liquid.

6. The method according to claim 5, wherein the density of the first liquid is at least approximately 1% greater than the density of the second liquid.

7. The method according to claim 4, wherein the first liquid comprises glycerol.

8. The method according to claim 1, wherein the density of the first liquid is greater than the density of the second liquid, and wherein the second liquid flows into the first liquid in a downward direction.

9. The method according to claim 8, wherein the density of the first liquid is at least approximately 0.3% greater than the density of the second liquid.

10. The method according to claim 9, wherein the density of the first liquid is approximately 1% greater than the density of the second liquid.

11. The method according to claim 8, wherein the first liquid comprises glycerol.

12. The method according to claim 11, wherein the glycerol concentration of the first liquid is from approximately 2.5% to less than approximately 25% glycerol.

13. The method according to claim 12, wherein the glycerol concentration of the first liquid is from approximately 5% to and including approximately 15% glycerol.

14. The method according to claim 1, wherein the chromatographic process is column chromatography and the solid support is a particulate.

15. The method according to claim 1, wherein the chromatographic process is membrane chromatography and the solid support is a porous membrane.

16. The method according to claim 1, wherein the elution pool volume is less than approximately 70% of the elution pool volume of the sample molecule in the control chromatography process.

17. A vertical column chromatographic method, without the need to use a moving packed bed adapter and without column inversion the method comprising:
   a) contacting with a solid support a first liquid containing a sample molecule and having a first physical characteristic;
   b) contacting with the first liquid a second liquid having a second physical characteristic;
   c) flowing the first and second liquids through the solid support;
   d) contacting with the second liquid a third liquid having a third physical characteristic and acts as an eluent of the sample molecule;
   e) flowing the second and third liquids through the solid support; and
   d) collecting the sample molecule in an elution pool volume;
       wherein the second liquid follows the first liquid and remains in contact with the first liquid;
       wherein the third liquid follows the second liquid and remains in contact with the second liquid;
       wherein the second physical characteristic of the second liquid and the third physical characteristic of the third liquid generate an interface between the second and third liquids such that mixing is minimized between the second and third liquids as they flow through the solid support; and wherein the elution pool volume is less than approximately 80% of the elution pool volume of the sample molecule in a control process analysis.

18. The method according to claim 17, wherein the method is an improvement over a control process, the improvement selected from the group consisting of reduced pool elution volume, increased purity of the sample molecule, and increased concentration of the sample molecule.

19. The method according to claim 18, wherein the physical characteristic is density.

20. The method according to claim 17, wherein the density of the second liquid is less than the density of the third liquid, and wherein third liquid flows into the second liquid in an upward direction.

21. The method according to claim 20, wherein the density of the second liquid is at least approximately 0.3% greater than the density of the third liquid.

22. The method according to claim 21, wherein the density of the second liquid is at least approximately 1% greater than the density of the third liquid.

23. The method according to claim 17, wherein the density of the second liquid is greater than the density of the third liquid, and wherein the third liquid flows into the second liquid in a downward direction.

24. The method according to claim 23, wherein the density of the second liquid is at least approximately 0.3% greater than the density of the third liquid.

25. The method according to claim 24, wherein the density of the second liquid is from approximately 1% greater than the density of the third liquid.

26. The method according to claim 17, wherein the second liquid comprises glycerol.

27. The method according to claim 26, wherein the glycerol concentration of the second liquid is from approximately 2.5% to less than approximately 25%.

28. The method according to claim 27, wherein the glycerol concentration is from approximately 5% to and including approximately 15%.

29. The method according to claim 17, wherein the chromatographic process is column chromatography and the solid support is a particulate.

30. The method according to claim 17, wherein the chromatographic process is membrane chromatography and the solid support is a porous membrane.

31. The method according to claim 17, wherein the elution pool volume is less than approximately 70% of the elution pool volume of the sample molecule in the control chromatography process.

* * * * *